United States Patent [19]

Fukuchi

[11] Patent Number: 5,004,909
[45] Date of Patent: Apr. 2, 1991

[54] METHOD AND APPARATUS FOR INSPECTING SIDEWALLS OF BOTTLES USING STRIPE PATTERN ILLUMINATION

[75] Inventor: Hiroyuki Fukuchi, Yokohama, Japan

[73] Assignee: Kirin Beer Kabushiki Kaisha, Tokyo, Japan

[21] Appl. No.: 357,265

[22] Filed: May 26, 1989

[30] Foreign Application Priority Data

May 30, 1988 [JP] Japan .................. 63-130154

[51] Int. Cl.$^5$ .............................................. G01N 9/04
[52] U.S. Cl. ............................ 250/223 B; 356/240
[58] Field of Search ................... 250/223 B, 225; 356/240, 239, 428, 376, 367, 368; 209/526, 524; 358/106

[56] References Cited

U.S. PATENT DOCUMENTS 4,376,951  3/1983  Miyazawa ........................ 358/106

FOREIGN PATENT DOCUMENTS 63-149547  6/1988  Japan .

Primary Examiner—David C. Nelms
Assistant Examiner—George Beck
Attorney, Agent, or Firm—Fleit, Jacobson, Cohn, Price, Holman & Stern

[57] ABSTRACT

A method and an apparatus for inspecting the sidewalls of bottles are disclosed. The sidewall of a bottle to be inspected is illuminated by a light in a pattern of stripes. At least three near points in an image of lights transmitted through the sidewall which are selected along a scan line are compared in brightness. When the central one of the three points to be noted has a brightness differing from the other near points on both sides of the noted point by more than a set value, the noted point is detected as a defect point. Based on the thus detected defect point, the presence of a defect on the sidewall of the bottle is judged. The method and the apparatus for inspecting the sidewalls of bottles can detect refractive defects as well as light-blocking defects with high precision.

40 Claims, 9 Drawing Sheets

DEFECT DETECTION SIGNAL

METHOD AND APPARATUS FOR INSPECTING SIDEWALLS OF BOTTLES USING STRIPE PATTERN ILLUMINATION

BACKGROUND OF THE INVENTION

This invention relates to a method and an apparatus for inspecting the sidewalls of bottles.

It is necessary to inspect glass bottles containing liquors, beverages, foods, etc. for defects whether the bottles are newly made or have been recovered. The bottles are inspected at various parts, i.e., the bodies or sidewalls, bottoms, tops of the mouths and the threaded bottle necks. Among these parts, the sidewalls tend to have defects such as foreign matters causing food sanitary problems, checks, cracks, scraches, seeds, blisters, etc., possibly causing accidental bottle breakages. Accordingly it is necessary to accurately identify and these defects to remove defective bottles with these defects. To this end there has been proposed a method for obtaining an image of light transmitted through a transparent or opaque bottle to detect defects based on a darkness distribution of the transmitted light image.

A problem with this method is that light-blocking defects, such as foreign matters, smears on the sidewall of a bottle, can be detected, based on a darkness distribution in an image of light transmitted through the sidewall. However based only on the darkness distribution, it is difficult to detect refractive defects, such as seeds, blisters, streaks, rumples, etc.

SUMMARY OF THE INVENTION

An object of this invention is to provide a method and an apparatus for inspecting the sidewalls of bottles which can detect the refractive defect as well as the light-blocking defect with high precision.

This object can be achieved by a method of inspecting the sidewalls of bottles comprising the steps of: illuminating the sidewall of a bottle by a light in a pattern of alternating shadowed and illuminated stripes; photoelectrically converting an image of light transmitted through the sidewall of the bottle; scanning the photoelectrically converted transmitted light image in the direction transverse to the stripes of the pattern; comparing in brightness at least three points near one another along the scan line; detecting as a defect point the central one of said at least three points when a brightness of the central point differs from brightnesses of the other ones of said at least three points on both sides of the central point by more than a set value; and judging the presence of a defect on the sidewall of the bottle, based on the detected defect point.

The above object and others can be achieved by providing an apparatus for inspecting the sidewalls of bottles comprising: illuminating means for illuminating the sidewall of a bottle by a light in a pattern of alternating shadowed and illuminated stripes; converting means for photoelectrically converting an image of light transmitted through the sidewall of the bottle illuminated by the illuminating means; defect detecting means for scanning the transmitted light image photoelectrically converted by the photoelectric means in the direction transverse to the stripes of the pattern to compare the brightness of at least three near points along the scan line, and detecting as a defect point the central point when a brightness of the central point differs from brightness of the other near points on both sides thereof by more than a set value; and judging means for judging the presence of a defect on the sidewall of the bottle, based on the defect point detected by the defect detecting means.

DETAILED DESCRIPTION OF THE INVENTION

Figure 1:
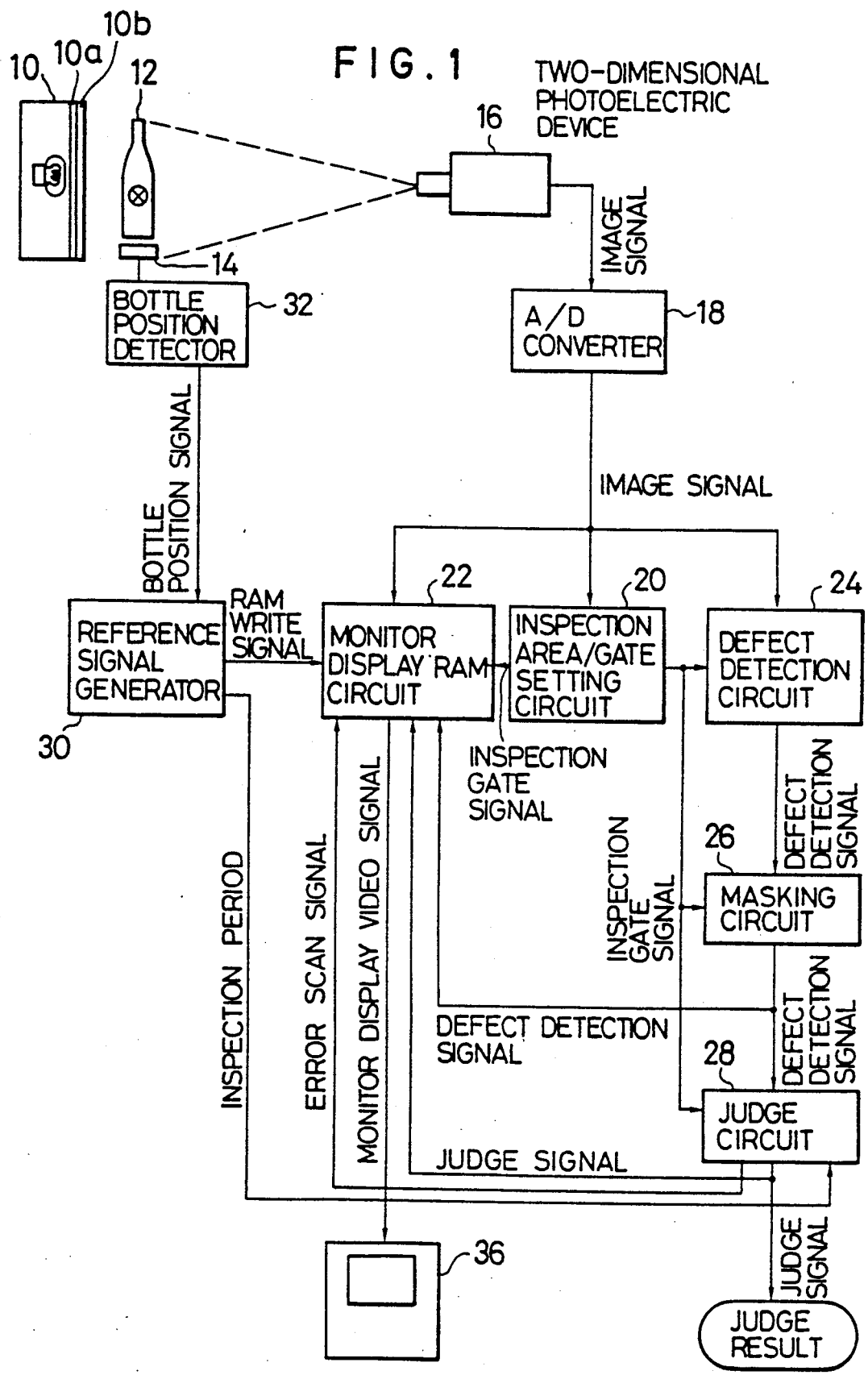
FIG. 1 is a block diagram of the apparatus for inspecting the sidewalls of bottles according to a first embodiment of this invention.
Figure 2:
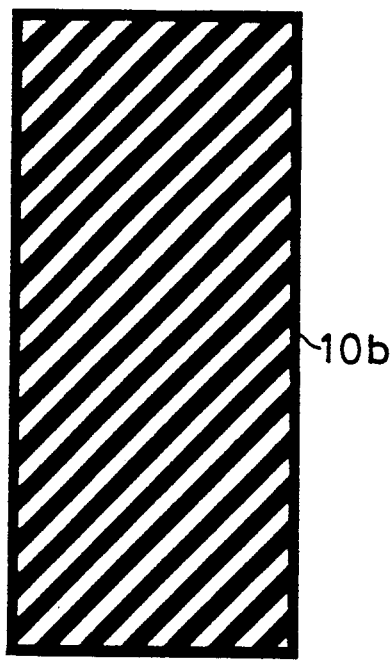
FIG. 2 is a view of a slant slit-plate used in the apparatus for inspecting the sidewalls of bottles according to the first embodiment.

FIG. 1 shows an apparatus for inspecting the sidewall of bottles according to a first embodiment of this invention. In the first embodiment, a bottle 12 is rotated on a rotary table 14. The bottle 12 is illuminated by a light source 10. The light source 10 has a diffusion plate 10a, and a slant slit-plate 10b provided on the front thereof. The diffusion plate 10a diffuses a light illuminated by the light source 10, and the slant slit-plate 10b splits the diffused light into a pattern of slant stripes alternating as shadowed or illuminated stripes as shown in FIG. 2. The bottle 12 is therefore illuminated by the light in a pattern of alternating dark and light slant stripes which has passed the slant slit-plate 10b.

Figure 3:
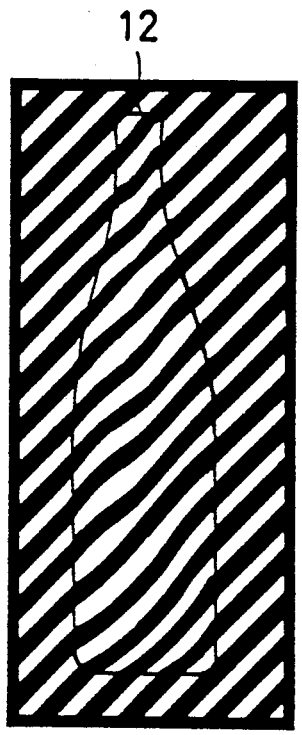
FIG. 3 is a view of an image of the lights transmitted through a bottle formed by the apparatus for inspecting the sidewalls of bottles according to the first embodiment.

An image of the light transmitted through the sidewall of the bottle 12 is formed in a two-dimensional photoelectric device 16, and a set number of the images are photoelectrically converted as the bottle 12 is being rotated. As shown in FIG. 3, the transmitted light image of the bottle 12 has distorted stripes at the parts corresponding to the edges of the bottle.

Figure 4A:
FIG. 4 are views of images of the light transmitted through defects of a bottle formed by the apparatus for inspecting the sidewalls of bottles according to the first embodiment.

As shown in FIG. 4(a), a light-blocking defect Fa on the bottle 12 appears in a dark point in a light one of the slant stripes of the pattern. This is due to the light obstructed by the light-blocking defect Fa. When the light-blocking defect Fa, appears as a dark point, in a dark one of the slant stripes of the pattern, the dark point cannot be discriminated from the dark stripe. But, as the bottle 12 is rotated, the light-blocking defect Fa appears in a light one of the slant stripes of the pattern. The light-blocking defect Fa, which cannot be detected in a dark one of the pattern of slant stripes, can be detected without failure when the light-blocking defect Fa comes into a light stripe.

Figure 4B:
Figure 4C:
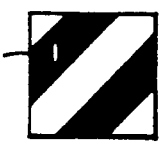

A refractive defect Fb on the bottle 12 appears as a light point in a light one of the slant stripes of the pattern as shown in FIG. 4(b) and appears in a light point in a dark one of the slant stripes of the pattern as shown in FIG. 4(c). This is caused by the stripes being distorted by the refractive defect Fb. When the refractive defect Fb occupies a large area, it often appears in a point which is reversed at the center as shown in FIG. 4(b).

Figure 4D:

An elongated refractive defect, such as streaks and rumples on the bottle 12, appears as a dark line in a light one of the pattern of slant stripes and as a light line in a dark one of the stripes as shown in FIG. 4(d).

An A/D converter 18 converts an analog image signal from the two-dimensional photoelectric device 16 into a digital image signal of a set number of bits. The digital image signal is supplied to an inspection area/gate setting circuit 20, a monitor display RAM circuit 22 and a defect detection circuit 14.

Figure 5:
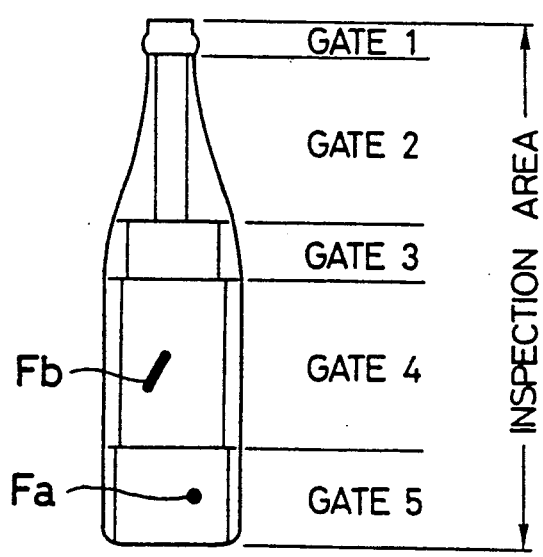
FIG. 5 is a view of inspection area and inspection gates used in the apparatus for inspecting the sidewalls of bottles according to the first embodiment.

The inspection area/gate setting circuit 20 is for determining, based on a transmitted light image of the bottle 12 as shown in FIG. 5, inspection areas where the defect detection circuit 24 detects defects. An inspection area is set between the top and the bottom edges of the transmitted light image of the bottle 12, and five inspection gates designated gates 1, 2, 3, 4 and 5 are set, based on the top and the bottom edges thereof. The inspection area/gate setting circuit 20 outputs an inspection gate signal to the monitor display RAM circuit 22, the defect detection circuit 24, a masking circuit 26 and a judge circuit 28. In the case where the edges of the transmitted light image of the bottle 12 is not clear-cut, it is possible to preset the inspection area and the inspection gates 1, 2, 3, 4 and 5 by the inspection area/gate setting circuit 20.

The defect detection circuit 24 detects defects based on a digital image signal from the A/D converter 18. During detection, a plurality of points in the direction oblique to the stripes in the longitudinal direction of the bottle 12, i.e., a plurality of points on a scan line along the rotational axis of the bottle 12, are compared in brightness.

In the defect detecting system used in this embodiment, a central or noted point A, and neighboring points B and C spaced from the point A by a set distance, are compared in brightness to detect whether or not the noted point A is a defect point. When the following relationships hold:

$$|QA - QB| \geq \text{(constant } A\text{)}$$

$$|QA - QC| \geq \text{(constant } A\text{)};$$

where the brightness at the points A, B and C are represented by QA, QB and QC a defect is present. The constant A is determined beforehand. In this defect detecting system, when the central of noted point A has a different brightness (darker or lighter) by a set value from the brightnesses of the near points B and C, the noted point A is taken as a defect point. This defect detecting system is free from erroneously detecting edges of the stripes of the pattern as defects and can detect accurately the light-blocking defect Fa and the refractive defect Fb without failure.

In the case where three points are in dark stripes of the pattern, the following formulas are satisfied:

$$QA1 - QB1 = 0$$

$$QA1 - QC1 = 0;$$

where the brightness of points A1, B1 and C1 are represented by QA1, QB1 and QC1. Accordingly the point A1 is not detected as a defect point.

In the case where three points A2, B2 and C2 are in a dark and a light stripe, the following formulas are satisfied:

$$QA2 - QB2 > A$$

$$QA2 - QC2 > 0;$$

where the brightness at the points A2, B2 and C2 are represented by QA2, QB2 and QC2. The point A2 is not detected as a defect point.

In the case where the three points A3, B3 and C3 are in a dark and a light stripe, the following formulas are satisfied:

$$QA3 - QC3 > A$$

$$QA3 - QB3 = 0;$$

where the brightness at the three points A3, B3 and C3 are represented by QA3, QB3 and QC3 hold. The point A3 is not detected as a defect point.

Figure 6:
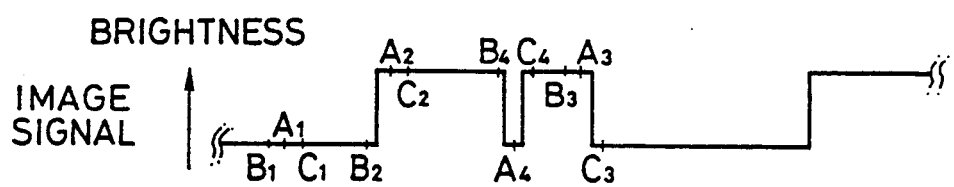
FIG. 6 is a view illustrating a defect detecting system used in the apparatus for inspecting the sidewalls of bottles according to the first embodiment.

As shown in FIG. 6, however, in the case where a defect appears as a dark point in a light one of the stripes of the pattern, and a noted point A4 is present in the stripe, the following formulas are satisfied:

$$QA4 - QB4 < -A$$

$$QA4 - QC4 < -A;$$

where the brightness at the three points A4, B4 and C4 are represented by AQ4, QB4 and QC4. The point A4 is detected as a defect point.

Figure 7:
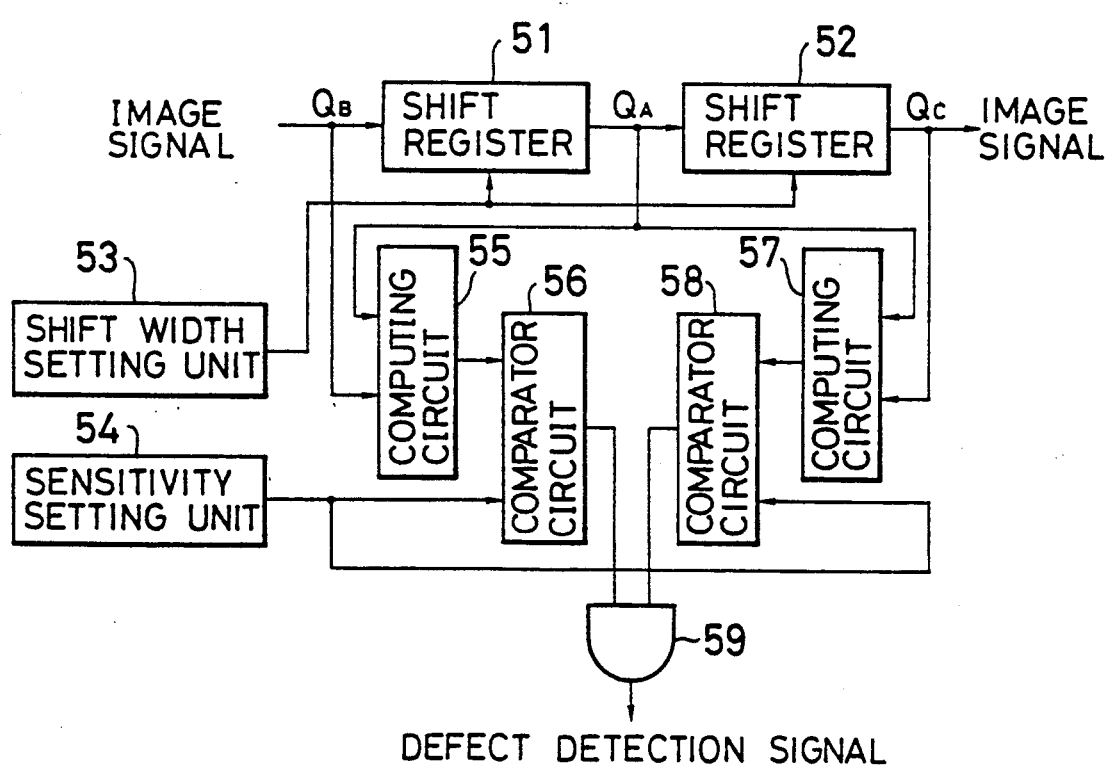
FIG. 7 is a block diagram of an example of a defect detection circuit for conducting the defect detecting system of FIG. 6.

An example of the defect detection circuit 24 is shown in FIG. 7. A digital image signal is input to a shift register 51 and the output therefrom is input to a shift register 52. The distance between one of the three points and the respective other two points depends on shift widths of the shift registers 51, 52. This shift width is determined by a shift width setting unit 53. In this example, the shift registers 51 and 52 have the same shift width.

A computing circuit 55 computes the absolute value of a difference between an output image signal QA of the shift register 51 and the input image signal QB thereto. The computed absolute value is compared by a comparator circuit 56 with a sensitivity (constant A) set by a sensitivity setting unit 54, which outputs a detection signal when the absolute value of the difference is larger than the constant A.

A computing circuit 57 computes the absolute value of a difference between an output image signal QC of the shift register 52 and the input image signal QA. The computed absolute value is compared by a comparator circuit 58 with the sensitivity (constant A) set by the sensitivity setting unit 54 and outputs a detection signal when the absolute value of the difference is larger than the constant A. The output signals from the comparator circuits 56 and 58 are input to an AND gate 59, and the AND gate outputs a defect detection signal when both output signals from the comparator circuits 56 and 58 are indicative of a defect.

Figure 8:
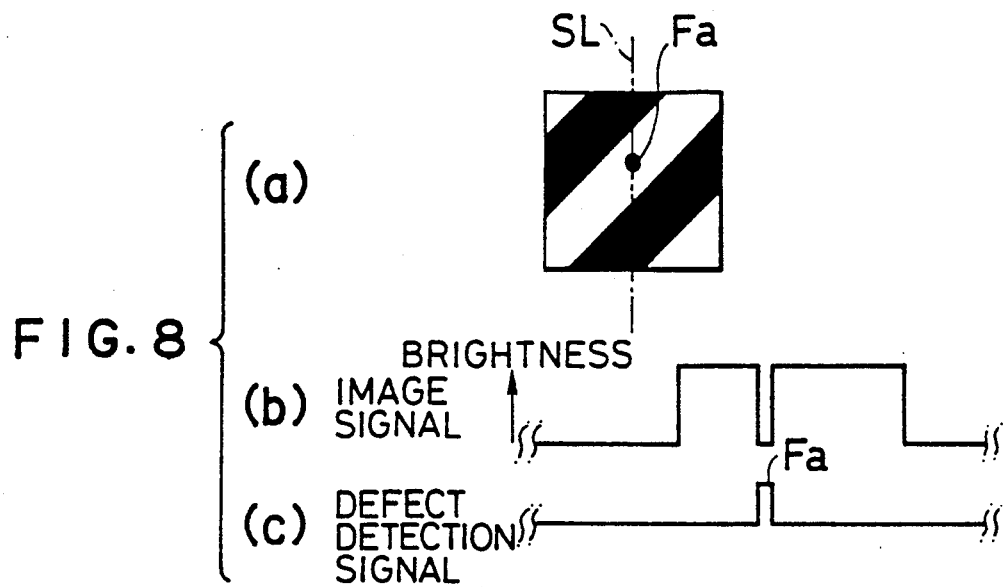
FIGS. 8-10 are views illustrating examples of the detection based on the defect detecting system of FIG. 6.
Figure 9:
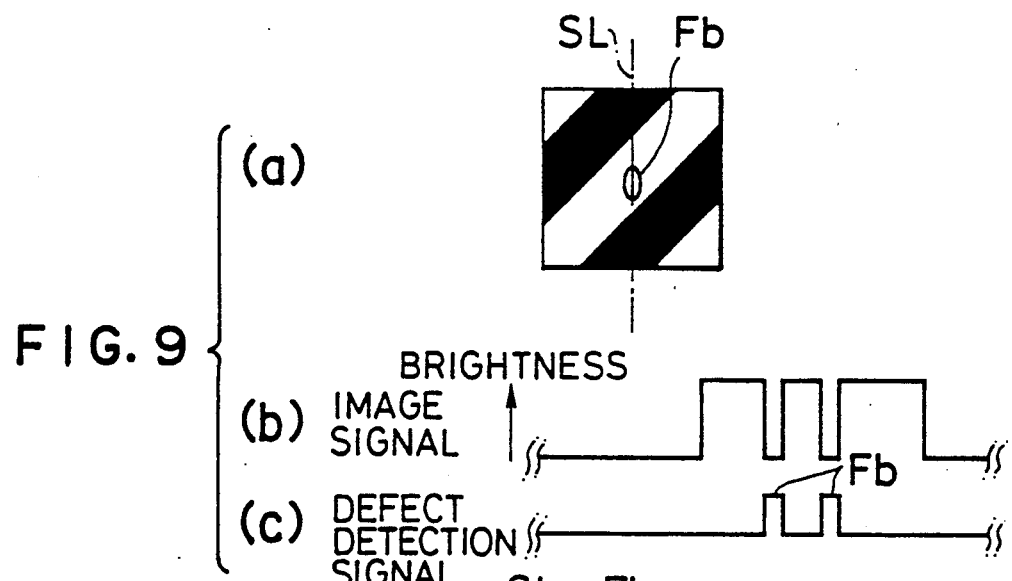
Figure 10:
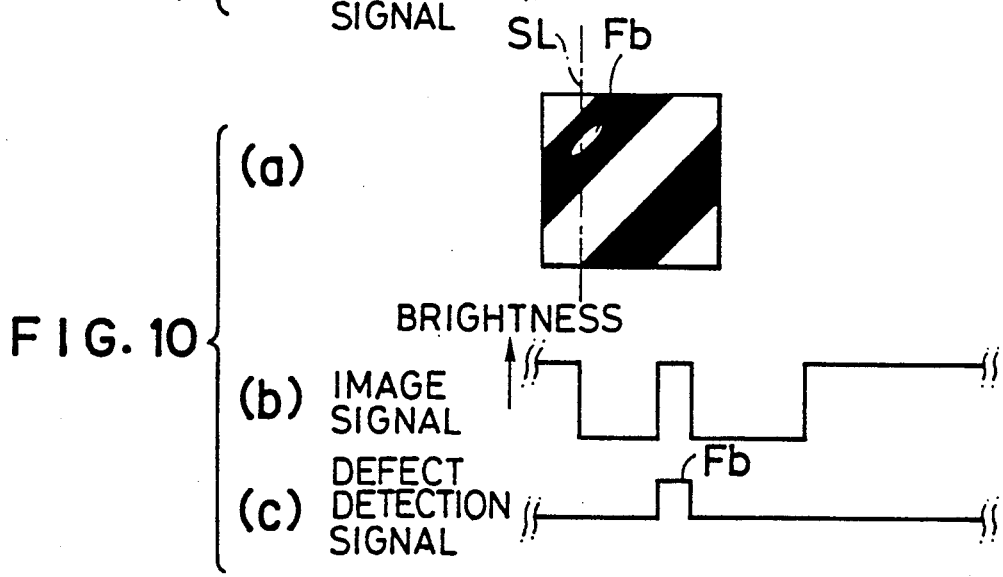

Examples of defect detection performed by the defect detection circuit 24 are shown in FIGS. 8–10.

FIG. 8 shows the case where a light-blocking defect Fa appears as a dark point in a light one of the stripes of the pattern. The brightness of an image signal along the scan line SL in FIG. 8(a) is as shown in FIG. 8(b). When the light-blocking defect Fa is detected by the above-described system, the defect Fa can be detected accurately as shown in FIG. 8(c).

FIG. 9 shows the case where a refractive defect Fb appears in a point having the dark outer periphery and the light center in a light one of the stripes of the pattern. The brightness of an image signal along the scan line SL in FIG. 9(a) is as shown in FIG. 9(b). When the refractive defect Fb is detected by the above-described defect detecting system, the defect Fb can be detected correctly as shown in FIG. 9(c).

FIG. 10 shows the case where a refractive defect Fb appears as a light point in a dark one of the stripes of the pattern. The brightness of an image signal along the scan line SL in FIG. 10(a) is as shown in FIG. 10(b). When the refractive defect Fb is detected by the above-described defect detecting system, the defect Fb can be detected correctly.

A defect detection signal output by the defect detection circuit 24 is masked by the masking circuit 26. When the sensitivity is increased for the prevention of erroneous detection of a defect by the defect detection circuit 24, sometimes non-defective points are erroneously detected as defects points. The masking removes such erroneous detection signals. The masking has various types. This embodiment uses a combination of continuous masking and area masking.

At a real defect, defect detection signals corresponding to the size of the defect are continuously output, but at normal points, detection signals are output separately. The continuous masking removes isolated defect detection signals and defect detection signals which continue only below a set value as not being actual defects.

The area masking is for removing noises caused when the sensitivity is increased so that light smears, streaks, rumples, seeds, blisters, etc., which have been missed by the conventional detection method, are detected. In the area masking a rectangular masking area centering a noted point is set, the defective points in the rectangular masking area are added to judge whether or not the sum of the defective points exceeds a set value, and, based on a judge result, an area masking signal is output. Accordingly an area masking signal is generated only at a portion where defective points are concentrated, and noises separately appearing are removed.

It is possible that the masking circuit 26 performs only one of the continuous masking and the area masking.

The judge circuit 28 judges the presence of a defect, based on defect detection signals clearing the masking by the masking circuit 26. For example, when a total number of defect detecting signals exceeds a set value, the bottle is judged defective. The judge signal is supplied to a conveyer unit (not shown) of the bottle 12, so that the conveyer unit removes the defective bottle based on the judge result.

A reference signal generating circuit 30 generates as output an inspection period signal, based on a bottle position signal from a bottle position detector 32. The inspection period signal is indicative of an inspection period and is supplied to the judge circuit 28. The judge circuit 28 takes as effective only the defect detecting signals generated in a period of time in which an inspection period signal is high level, to judge whether or not the bottle 12 is a defective bottle. It is also possible to output an inspection period signal to the inspection area/gate setting circuit 20, the defect detection circuit 24 and the masking circuit 26, and take as effective only the defect detection signals generated in a period of time in which an inspection period signal is high.

The monitor display RAM 22 stores digital image signals of the bottle 12 at a built-in frame memory and displays an image on a monitor 36. The monitor display RAM circuit 22 receives a defect detection signal from the masking circuit 26, a judge result signal from the judge circuit 28, and an inspection gate signal from the inspection area/gate setting circuit 20. A defect point is written in the monitor display RAM circuit 22, based on a defect detection signal. An inspection gate is indicated on the monitor, based on an inspection gate signal.

It is possible that the monitor display RAM circuit 22 has two frames, and the two frames are used alternately to store a current photoelectrically converted digital image signal and a preceding photoelectrically converted digital image signal.

According to this embodiment, a bottle is illuminated by a striped pattern light formed by the slant slit-plate, so that not only the light-blocking defect but also the refractive defect can be detected with high sensitivity.

A defect detecting system used in the apparatus for inspecting the sidewalls of bottles according to a second embodiment of this invention will be explained with reference to FIG. 11.

The defect detecting system used in the second embodiment is effective for the case in which a transmitted light image has an uneven distribution of brightness due to an uneven saturation of a color, etc.

What is common with the system used in the first embodiment is that three points, i.e., a noted point A, and near points B and C spaced from the noted point A by a set distance are selected to compare the three points A, B, C in brightness so as to judge whether or not the noted point A is a defect point.

What differs in the system according to the second embodiment from the system used in the first embodiment is that in the latter a defect is judged, only based on the absolute value of a difference among brightnesses QA, QB and QC of the respective points A, B and C, while the former uses information that the noted point A is brighter or less bright than the neighboring points B and C.

In this embodiment, only when a brightness QA of the noted point A is higher than the brightness QB, QC of the near points B, C, or when the brightness QA of the noted point A is lower than the brightness QB, QC of the near points B, C, the noted point A is detected as a defect. In the case where a brightness QA of the noted point A is higher than that QB of the position B but lower than that QC of the point C, the noted point A is not detected as a defect point even though the absolute values of differences are above a constant A.

That is, when the following formulas are satisfied:

$QA - QB \geq$ (constant $A$)

$QA - QC \geq$ (constant $A$);

the point A is detected as a defect point when the following formulas are satisfied:

$QA - QB < -$(constant A)

$QA - QC < -$(constant A);

the point A is detected as a defect point.
When the following formulas are satisfied:

$QA - QB \geq$ (constant $A$)

$QA - QC < -$(constant A);

the noted point A is not detected as a defect point also, when the following formulas are satisfied:

$QA - QB < -$(constant A)

$QA - QC \geq$ (constant $A$);

the noted point A is not detected as a defect point.

Figure 11:
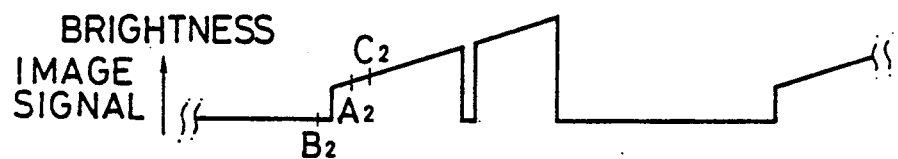
FIG. 11 is a view illustrating a defect detecting system used in the apparatus for inspecting the sidewalls of bottles according to a second embodiment of this invention.

Thus, even in the case of uneven brightness as in FIG. 11, a defect can be judged correctly. That is, even though the absolute values are above a constant A, as the noted point A is brighter than the near point B but less bright than the near point C, the noted point A is correctly judged not to be a defect point.

Figure 12:
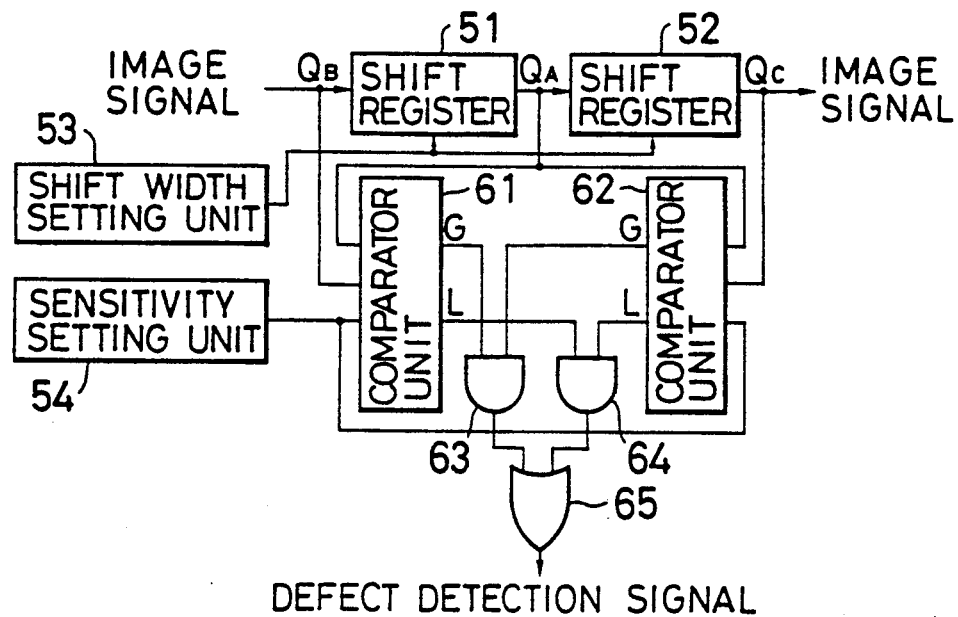
FIGS. 12 and 13 are block diagrams of an example of a defect detection circuit for use in the apparatus for inspecting the sidewalls of bottles according to the second embodiment.

FIG. 12 shows a block diagram of an example of the defect detection circuit 24 for use in this embodiment. Members common between FIGS. 7 and 12 share the same reference numerals.

An input image signal QB and the output image signal QA are compared by a comparator unit 61 to judged whether or not the absolute value of a difference between the two image signals is larger than a set value S of a sensitivity setting circuit 54 and whether or not the output image signal QA is brighter than the input image signal QB. When the output image signal QA is brighter than the input image signal QB by more than a set value, an output signal G achieves a high level H, and when the output image signal QA is less brighter than the input image signal QB by more than a set value S, an output signal G achieves a low level L.

Figure 13:
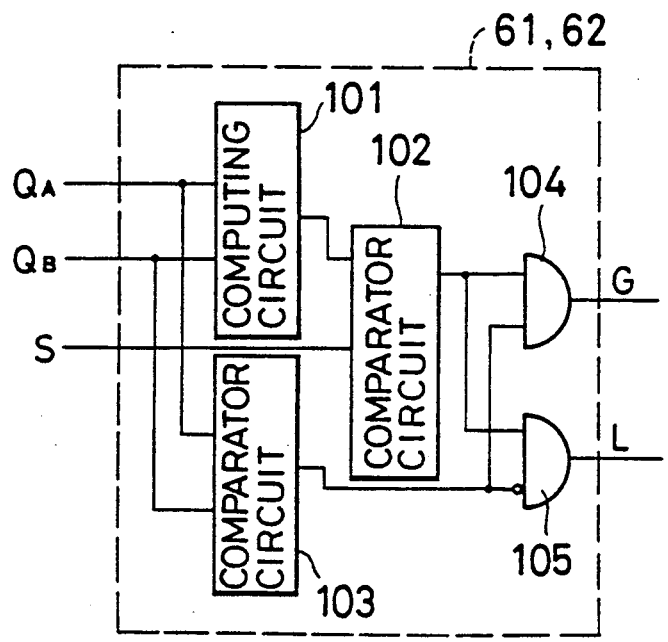

The comparator unit 61 is shown in FIG. 13 in detail. A computing circuit 101 computes the absolute value of a difference between an image signal QA and an image signal QB. A computation result is compared with the set value S in a comparator circuit 102. A comparator circuit 103 compares image signals QA and QB to judge which is brighter. An AND gate 104 is provided and receives an output signal from the comparator circuit 102 and an output signal from the comparator circuit 103 to output a signal G of a logical product between the two. The output signal G achieves high level H when the comparator circuit 102 finds that an absolute value of the difference between the image signals QA and QB is larger than the set value, and the image signal QA is brighter than the image signal QB. An AND gate 105 is supplied with an output signal of the comparator circuit 102 and the inversed signal of an output signal of the comparator circuit 103 to output a signal L of a logical product between the two. The signal L achieves a high level H when the comparator circuit 102 finds that an absolute value of the difference between the image signals QA and QB is larger than a set value S, and further that the image signal QA is less bright than the image signal QB.

Figure 14:
FIG. 14 is a view illustrating a defect detecting system for use in the apparatus for inspecting the sidewalls of bottles according to a third embodiment of this invention.

A defect detecting system for the apparatus for inspecting the sidewalls of bottles according to a third embodiment of this invention will be explained with reference to FIG. 14.

In the first and the second embodiments described above, a noted point A, and two near points B and C interposing the noted point A are selected for the judgement of a defect. In this third embodiment, however, as shown in FIG. 14, a noted point A, a couple of near points B and D on one side of the noted point A, and another couple of near points C and E on the other side of the noted point A are selected for the judgement of a defect.

The defect detecting system for a first form of this third embodiment is based on the same principle as the systems for the first embodiment. The noted point A is compared with the near points B and D and with the near points C and E in brightness. When the noted point A has a brightness different from one of the near points B and D by more than a set value, and the noted point A has a brightness different from one of the near points C and E by more than the set value, the noted point A is detected as a defect point.

That is, the noted point A is detected as a defect point when the following formulas are satisfied:

$|QA - (QB \text{ or } QD)| \geq$ (constant $A$)

$|QA - (QC \text{ or } QE)| \geq$ (constant $A$):

where brightnesses at the respective points A, B, C, D, and E are represented by QA, QB, QC, QD and QE.

According to the defect detecting system for the this embodiment, even when a defect has been missed since the size of the defect coincides with a distance between one of the near point and a noted point, the defect can be detected, based on the other near points.

Figure 15:
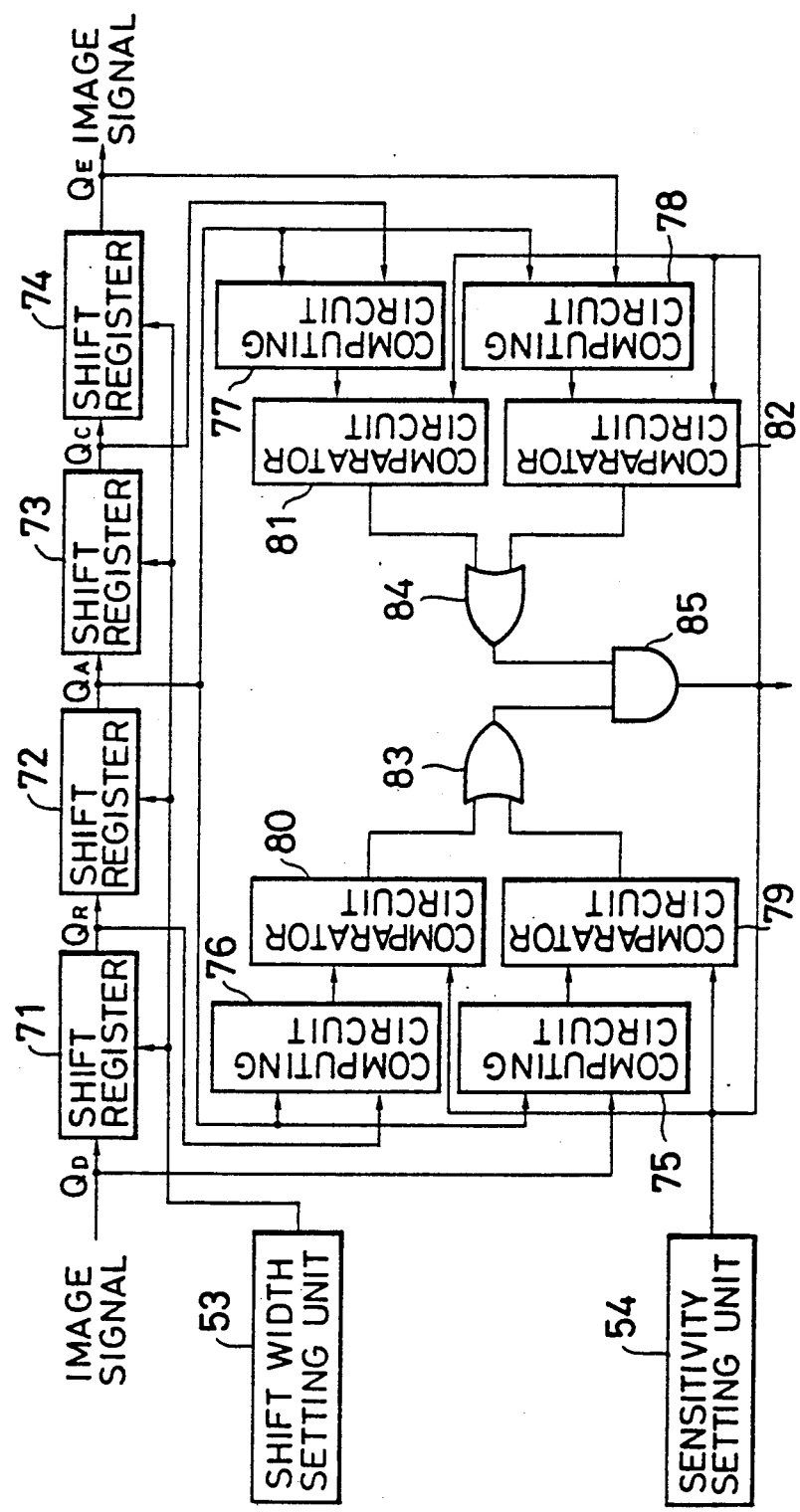
FIG. 15 is a block diagram of an example of a defect detection circuit for use in the apparatus for inspecting the sidewalls of bottles according to the third embodiment.

FIG. 15 shows a block diagram of an example of the defect detection circuit for use in this embodiment.

An image signal is input consecutively to four shift registers 71–74. Respective shift registers 71, 72, 73, 74 are associated with respective computing circuits 75, 76, 77, 78 and respective comparator circuits 79, 80, 81, 82. The computing circuits 75, 76, 77, 78 judge whether the absolutes values of differences of the noted point A and the respective near points B, C, D, E are larger than a set value of a sensitivity setting circuit 54. An OR gate 83 is supplied with outputs of the comparators 79, 80 to give a logical sum of the two. An OR gate 84 is supplied with outputs of the comparators 81, 82 to give a logical sum of the two. An AND gate 85 gives a logical product of outputs of the OR gates 83, 84.

It is also possible that the defect detecting system for this embodiment is based on the same principle as that for the second embodiment. That is, a noted point A is detected as a defect only when a brightness QA of the noted point A is higher or lower than brightnesses QB (or QD) and QC (or QE) of a near points B (or D) and a near point C (or E). When a brightness QA of the noted point A is higher than that of a near point B (or D) but lower than that of a near point C (or E), the noted point A is not detected as a defect point even though the absolute values of the differences are larger than a constant A.

That is, a noted point A is detected as a defect point when the following formulas are satisfied:

$$QA-(QB \text{ or } QD) \geq (\text{constant } A)$$

$$QA-(QC \text{ or } QE) \geq (\text{constant } A);$$

or when the following formulas are satisfied:

$$QA-(QB \text{ or } QD) < -(\text{constant } A)$$

$$QA-(QC \text{ or } QE) < -(\text{constant } A).$$

Thus, even in the case of uneven brightness as in FIG. 11, a defect can be detected correctly.

Figure 16:
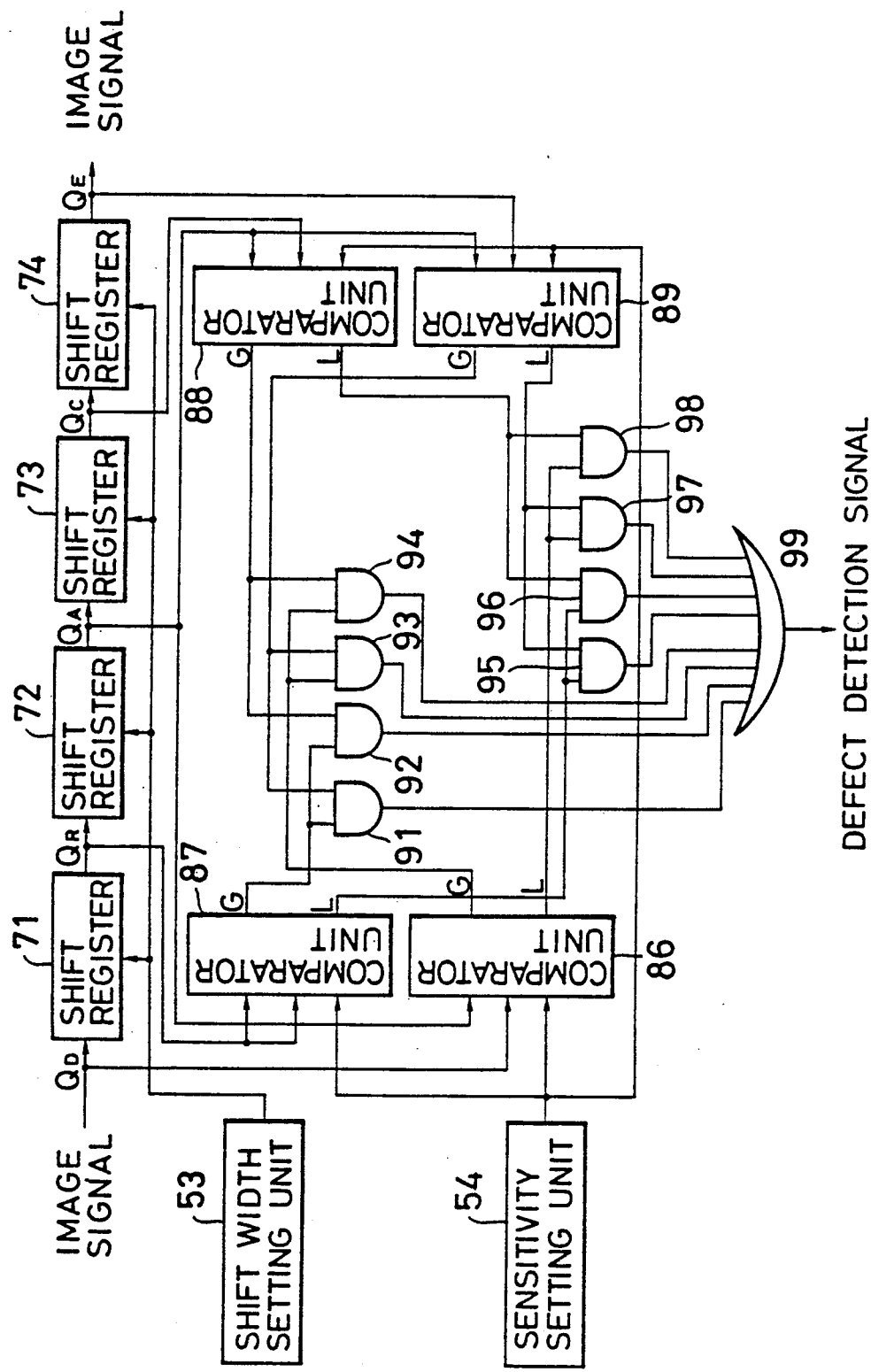
FIG. 16 is a block diagram of another example of a defect detection circuit for use in the apparatus for inspecting the sidewalls of bottles according to the third embodiment.

FIG. 16 is a block diagram of another example of the defect detection circuit 24 for this defect detecting system.

Respective shift registers 71, 72, 73, 74 are associated with respective comparator units 86, 87, 88, 89 of FIG. 13. The comparator units 86, 87, 88, 89 judge whether a noted point A is brighter than respective near points B, C, D and E by more than a set value of a sensitivity circuit 54. AND gates 91, 92, 93, 94 give logical products of output signals G of the comparator units 86–89. The AND gate 91 gives a logical product of the outputs signals G of the comparator units 87, 89. The AND gate 92 gives a logical product of the output signals G of the comparator units 87, 88. The AND gate 93 gives a logical product of output signals G of the comparator units 86, 89. The AND gate 94 gives a logical product of outputs signals G of the comparators 86, 88. AND gates 95, 96, 97, 98 give a logical product of output signals L of the comparator units 86, 87, 88, 89. The AND gate 95 gives a logical product of output signals L of the comparator units 87, 89. The AND gate 96 gives a logical product of output signals L of the comparator units 87, 88. The AND gate 97 gives a logical product of outputs L of the comparator units 86, 89. The AND gate 98 gives a logical product of output signals L of the comparator units 86, 88. An OR gate 99 gives a logical sum of outputs of the AND gates 91–94 and 95–98 to output the logical sum as a defect detection signal.

Figure 17:
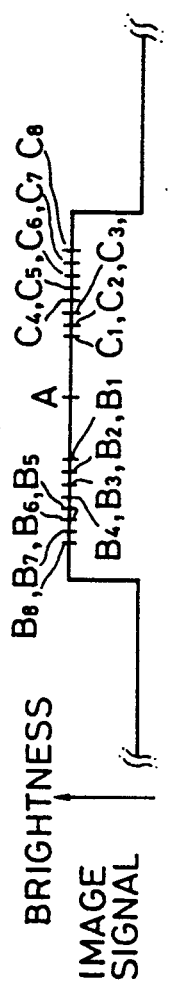
FIG. 17 is a view illustrating a defect detecting system for use in the apparatus for inspecting the sidewalls of bottles according to a fourth embodiment of this invention.

A defect detection system used in the apparatus for inspecting the sidewalls of bottles according to a fourth embodiment of this invention will be explained with reference to FIG. 17.

In the first and the second embodiments, a noted point A, and two points near the noted point A are selected to judge whether the noted point A is a defect point. In this embodiment, however, as shown in FIG. 17, a noted point A, and a plurality of near points B1-B8 (8 points in this embodiment) on one side of the noted point A and a plurality of near points C1-C8 (8 points in this embodiment) on the other side of the noted point A are selected. This embodiment elongates the extent of detection by selecting two sets of 8 near points B1-B8 and C1-C8 instead of two near points as in the first and the second embodiments.

It is preferable that the distance between a near point B8 and a near point C8 is smaller than a width of the stripes of the pattern.

A defect detecting system for this fourth embodiment is based on the same principle as that for the first embodiment. A noted point A and respective near points B1-B8 are compared in brightness, and the noted point A and respective near points C1-C8 are compared in brightness. The noted point A is detected as a defect point when a brightness QA of the noted point A differs from that QB1-QB8 of the near points B1-B8 by more than a set value, and further a brightness QA of the noted point A differs from that QC1-QC8 of the near points C1-C8 by more than a set value.

Figure 18:
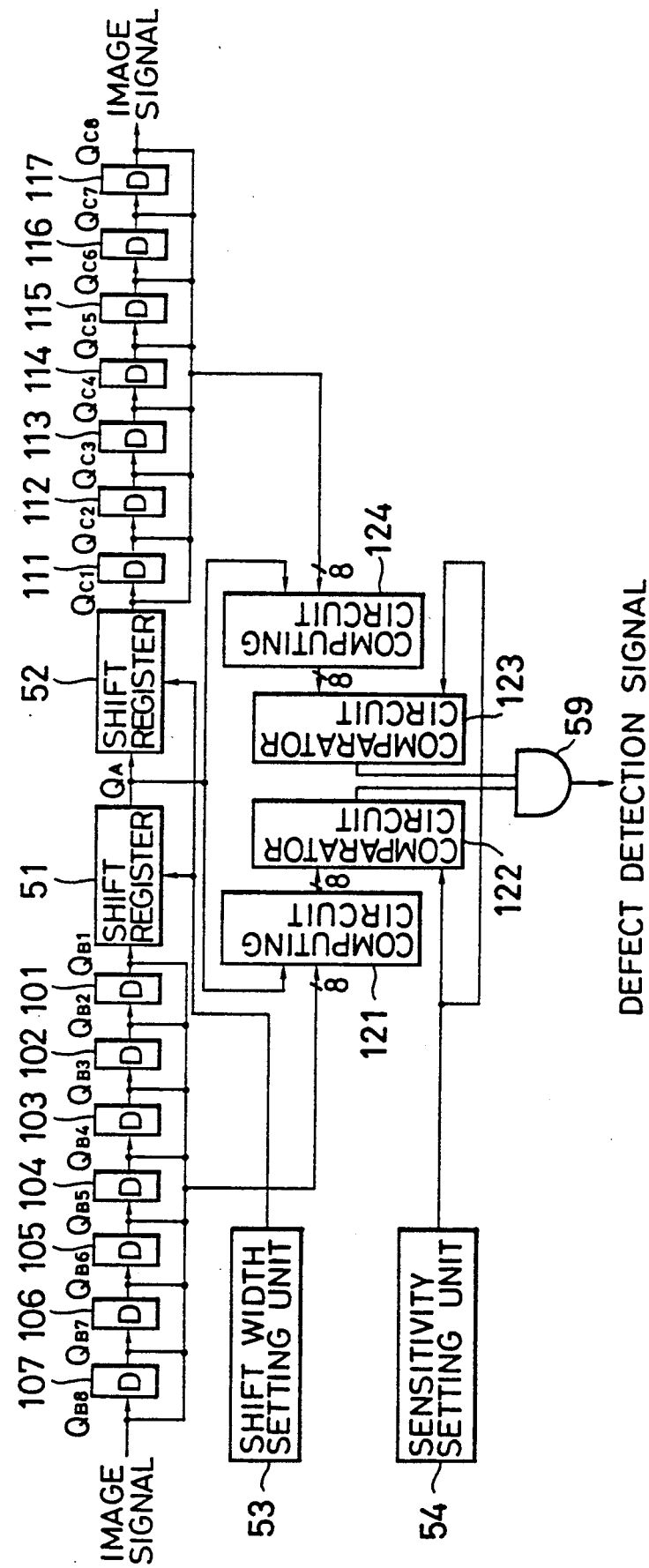
FIG. 18 is a block diagram of an example of a defect detecting circuit for use in the apparatus for inspecting the sidewalls of bottles according to the fourth embodiment.

FIG. 18 shows a block diagram of an example of a defect detection circuit 24 of the apparatus for inspecting the sidewalls of bottles according to this embodiment.

An image signal is input consecutively to 7 flip-flops 101-107, shift registers 51 and 52 and D flip-flops 111-117. A computing circuit 121 computes the absolute values of differences between brightnesses QB1-QB8 of respective near points B1-B8 and a brightness QA of a noted point A. A comparator circuit 122 judges whether the absolute values of the respective differences given by the computing circuit 121 are larger than a set value of a sensitivity setting circuit 54. A computing circuit 124 computes the absolute values of differences between the brightnesses QC1-QC8 of the respective near points and the brightness QA of the noted point A. A comparator circuit 123 judges whether or not the absolute values of the respective differences are larger than the set value of the sensitivity circuit 54. An AND gate 59 gives a logical product of outputs of the comparator circuits 122, 123.

A defect detecting system for this embodiment may be based on the same principle as that for the second embodiment. That is, only when a brightness QA of a noted point A is higher than brightnesses QB1-QB8 of near points B1-B8 and those QC1-QC8 of near points C1-C8, or when the brightness QA of the noted point A is lower than the brightnesses QB1-QB8 of near points B1-B8 and QC1-QC8 of near points C1-C8, is the noted point A is detected as a defect point. When the noted point A is brighter than the near points B1-B8 but less bright than the near points C1-C8, the noted point A is not detected as a defect even though all the absolute values of the differences are larger than a constant A.

Thus, even in the case of uneven brightness as in FIG. 11, a defect can be detected correctly.

Figure 19:
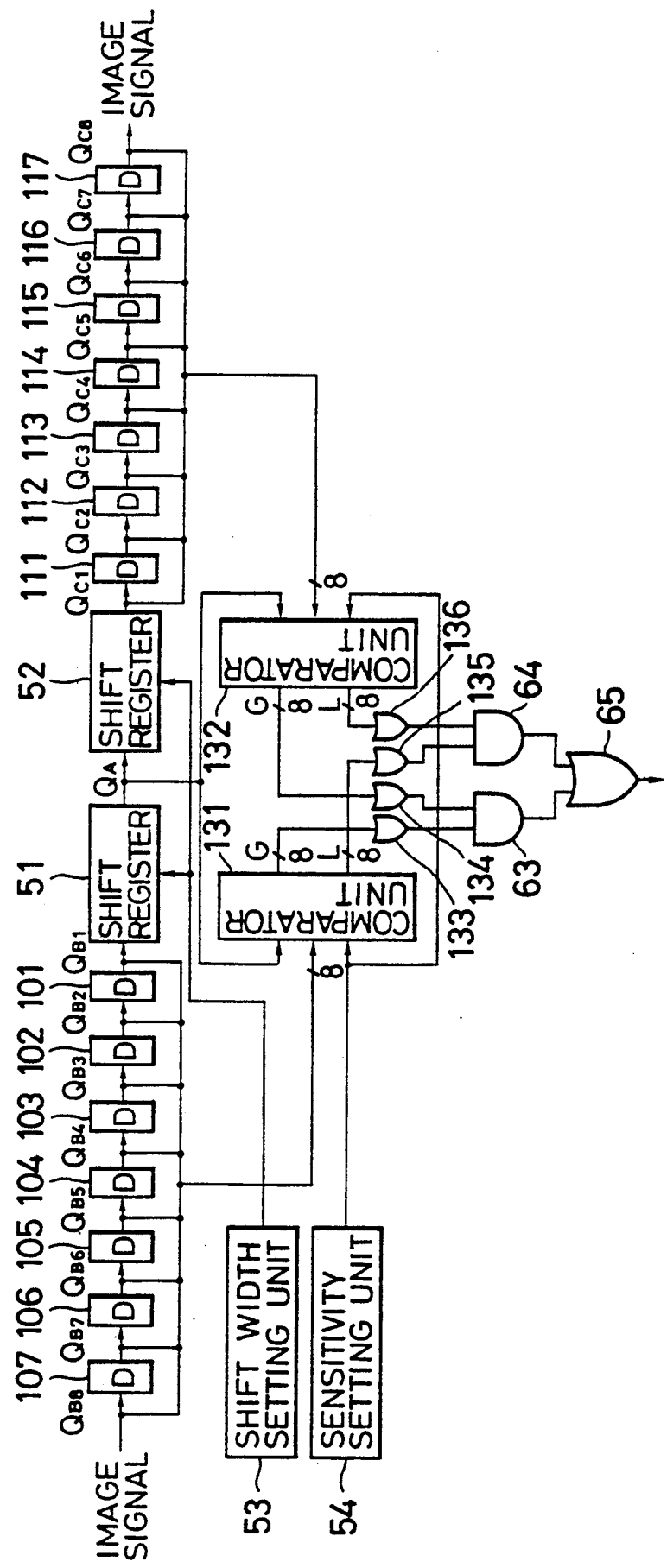
FIG. 19 is a block diagram of another example of a defect detecting circuit for use in the apparatus for inspecting the sidewalls of bottles according to the fourth embodiment.

FIG. 19 shows another example of a defect detection circuit 24 for the defect detecting system used in this embodiment.

Respective shift registers 51, 52 are associated with respective comparator units 131, 132. The comparator units 131, 132 judge whether or not a noted point A is brighter than near points B1–B8 and C1–C8 by more than a set value. OR gates 133, 134 give logical sums of output signals G of the comparator units 131, 132, and then an AND gate 63 gives a logical product of the two OR gates 133 and 134. OR gates 135, 136 give a logical sum of output signals L of the comparator units 131, 132, and then an AND gate 64 gives a logical product of the two OR gates 135 and 136. An OR gate 65 gives a logical sum of outputs of the AND gates 63, 64 to be output as a defect detection signal.

This invention is not limited to the above-described embodiment and covers various modifications in addition to the above-described embodiments.

According to this invention, near points may be in any number more than two. The distance between a noted point and each near point, and the distance between the near points may be arbitrarily determined.

In the above-described embodiments, the bottle 12 is rotated at a fixed position but may be continuously moved on rotation. In the latter case it is possible to inspect the bottle 12 by installing a vibratory lens or a vibratory mirror.

In the above-described embodiments, in order to detect a brightness difference between two points, a difference in brightness between the two is computed, but instead it is possible that a division between the two is made by the computing circuit to give a ratio and to compare the ratio with a set value.

In the above-described embodiments, a pattern of straight stripes is used, but the stripes may be curved.

In the above-described embodiments, the stripes are oblique to a rotation axis of a bottle, but the stripes may be perpendicular to a rotation axis of a bottle. In this case, one bottle is twice inspected, firstly by a pattern of stripes and secondly by a pattern of the reverse stripes.

In the above-described embodiments, the diffusion plate and slant slit-plate are separate, but the diffusion plate may have a striped pattern formed integral therewith.

A bottle to be inspected may be made of transparent glass, opaque glass or plastics. This invention is applicable to the sidewalls of glass containers and glass panes.

What is claimed is:

1. A method of inspecting the sidewalls of bottles comprising the steps of:
   illuminating the sidewall of a bottle by light in a pattern of alternating shadowed and illuminated stripes to transmit an image of alternating dark and light stripes therethrough;
   photoelectrically converting the image transmitted through the sidewall of the bottle;
   scanning the photoelectrically converted transmitted light image along a scan line in a direction transverse to the dark and light stripes;
   sensing the brightness at at least three points near one another along said scan line, said at least three points comprising a central point and outer points on both sides of said central point;
   comparing the brightness of said at least three points with each other;
   detecting a defect point at said central one of said at least three points when the brightness of the central point differs from the brightness of each of the outer points on both sides of the central point by more than a set value; and
   judging the presence of a defect on the sidewall of the bottle based on the defect point.

2. A method of inspecting the sidewalls of bottles according to claim 1, wherein the dark and light stripes are oblique to a rotation axis of the bottle.

3. A method of inspecting the sidewalls of bottles according to claim 1, wherein said step of detecting a defect point detects the central point as a defect point when the brightness of the central point is greater than the brightness of each of the outer points by more than said set value, or when the brightness of the central point is less than the brightness of each of the outer points by more than said set value.

4. A method of inspecting the sidewalls of bottles according to claim 2, wherein said step of detecting a defect point detects said central point as a defect point when the brightness of the central point is greater than the brightness of each of the outer points by more than said set value, or when the brightness of the central point is less than the brightness of each of the outer points by more than said set value.

5. A method of inspecting the sidewalls of bottles according to claim 1, and further comprising the steps of:
   selecting first and second sets each comprising a plurality of points along said scan line, said first and second sets being on opposite sides of said central point;
   performing said step of comparing said central point with respect to points in said first and second set similarly positioned distant from said central point but on opposite sides of said central point;
   performing said step of detecting a defect point with respect to each one of the points in each of said first and second sets; and
   designating said central point a defect point with respect to said first and second sets of points if said central point is determined to be a defect point with respect to any one of said points in each of said first and second sets.

6. A method of inspecting the sidewalls of bottles according to claim 2, and further comprising the steps of:
   selecting first and second sets each comprising a plurality of points along said scan line, said first and second sets being on opposite sides of said central point;
   performing said step of comparing said central point with respect to points in said first and second set similarly positioned distant from said central point but on opposite sides of said central point;
   performing said step of detecting a defect point with respect to each one of the points in each of said first and second sets; and
   designating said central point a defect point with respect to said first and second sets of points if said central point is determined to be a defect point with respect to any one of said points in each of said first and second sets.

7. A method of inspecting the sidewalls of bottles according to claim 3, and further comprising the steps of:
   selecting first and second sets each comprising a plurality of points along said scan line, said first and second sets being on opposite sides of said central point;
   performing said step of comparing said central point with respect to points in said first and second set similarly poistioned distant from said central point but on opposite sides of said central point;

performing said step of detecting a defect point with respect to each one of the points in each of said first and second sets; and designating said central point a defect point with respect to said first and second sets of points if said central point is determined to be a defect point with respect to any one of said points in each of said first and second sets.

8. A method of inspecting the sidewalls of bottles according to claim 4, and further comprising the steps of:

selecting first and second sets each comprising a plurality of points along said scan line, said first and second sets being on opposite sides of said central point;

performing said step of comparing said central point with respect to points in said first and second set similarly positioned distant from said central point but on opposite sides of said central point;

performing said step of detecting a defect point with respect to each one of the points in each of said first and second sets; and designating said central point a defect point with respect to said first and second sets of points if said central point is determined to be a defect point with respect to any one of said points in each of said first and second sets.

9. A method of inspecting the sidewalls of bottles according to claim 1, wherein:

a distance between said outer points is less than a width of the dark and light stripes.

10. A method of inspecting the sidewalls of bottles according to claim 2, wherein:

a distance between said outer points is less than a width of the dark and light stripes.

11. A method of inspecting the sidewalls of bottles according to claim 3, wherein:

a distance between said outer points is less than a width of dark and light stripes.

12. A method of inspecting the sidewalls of bottles according to claim 4, wherein:

a distance between said outer points is less than a width of the dark and light stripes.

13. A method of inspecting the sidewalls of bottles according to claim 5, wherein:

a distance between points in each of said first and second sets most distant from said central point is less than a width of the dark and light stripes.

14. A method of inspecting the sidewalls of bottles according to claim 6, wherein:

a distance between points in each of said first and second sets most distant from said central point is less than a width of the dark and light stripes.

15. A method of inspecting the sidewalls of bottles according to claim 7, wherein:

a distance between points in each of said first and second sets most distant from said central point is less than a width of the dark and light stripes.

16. A method of inspecting the sidewalls of bottles according to claim 8, wherein:

a distance between points in each of said first and second sets most distant from said central point is less than a width of the dark and light stripes.

17. An apparatus for inspecting the sidewalls of bottles comprising:

illuminating means for illuminating the sidewall of a bottle by a light in a pattern of alternating shadowed and illuminated stripes for transmitting an image of alternating dark and light stripes therethrough;

converting means for photoelectrically converting said image transmitted through the sidewall of the bottle by the illuminating means;

scanning means for scanning the image photoelectrically converted by the converting means along a scan line in a direction transverse to the dark and light stripes;

sensing means for sensing the brightness at least three points near one another along said scan line, said at least three points being designated a central point and outer points on both sides of said central point;

comparing means for comparing the brightness at said at least three points along the scan line with each other;

defect detecting means for detecting a defect point at the central point when a brightness of the central point differs from the brightness of each of the outer points on both sides of the central point by more than a set value; and judging means for judging the presence of a defect on the sidewall of the bottle based on the defect point detected by the defect detecting means.

18. An apparatus for inspecting the sidewalls of bottles according to claim 17, wherein the dark and light stripes formed by the illuminating means are oblique to a rotation axis of the bottle.

19. An apparatus for inspecting the sidewalls of bottles according to claim 17, wherein the defect detecting means detects said central point as said defect point when the brightness of the noted point is greater than the brightness of each of the outer points, or when the brightness of the central point is less than the brightness of each of the outer points.

20. An apparatus for inspecting the sidewalls of bottles according to claim 18, wherein the defect detecting means detects said central point as said defect point when the brightness of the noted point is greater than the brightness of each of the outer points, or when the brightness of the central point is less than the brightness of each of the outer points.

21. An apparatus for inspecting the sidewalls of bottles according to claim 17, and further comprising:

means for selecting first and second sets each comprising a plurality of points, said first and second sets being on opposite sides of said central point; and wherein the defect detecting means detects said central point as a defect point when said central point is detected as a defect point with respect to any one of said points in each of said first and second sets.

22. An apparatus for inspecting the sidewalls of bottles according to claim 18, and further comprising:

means for selecting first and second sets each comprising a plurality of points, said first and second sets being on opposite sides of said central point; and wherein the defect detecting means detects said central point as a defect point when said central point is detected as a defect point with respect to any one of said points in each of said first and second sets.

23. An apparatus for inspecting the sidewalls of bottles according to claim 19, and further comprising:

means for selecting first and second sets each comprising a plurality of points, said first and second sets being on opposite sides of said central point; and wherein the defect detecting means detects said central point as a defect point when said central point is detected as a defect point with respect to any one of said points in each of said first and second sets.

24. An apparatus for inspecting the sidewalls of bottles according to claim 20, and further comprising:

means for selecting first and second sets each comprising a plurality of points, said first and second sets on opposite sides of said central point; and wherein the defect detecting means detects said central point as a defect point when said central point is detected as a defect point with respect to any one of said points in each of said first and second sets.

25. An apparatus for inspecting the sidewalls of bottles according to claim 17, wherein a distance between the outer points is less than a width of the dark and light stripes.

26. An apparatus for inspecting the sidewalls of bottles according to claim 18, wherein a distance between the outer points is less than a width of the dark and light stripes.

27. An apparatus for inspecting the sidewalls of bottles according to claim 19, wherein a distance between the outer points is less than a width of the dark and light stripes.

28. An apparatus for inspecting the sidewalls of bottles according to claim 20, wherein a distance between said outer points is less than a width of the dark and light stripes.

29. An apparatus for inspecting the sidewalls of bottles according to claim 21, wherein a distance between the points in each of said first and second sets most distant from said central point is less than a width of the dark and light stripes.

30. An apparatus for inspecting the sidewalls of bottles according to claim 22, wherein a distance between the points in each of said first and second sets most distant from said central point is less than a width of the dark and light stripes.

31. An apparatus for inspecting the sidewalls of bottles according to claim 23, wherein a distance between the points in each of said first and second sets most distant from said central point is less than a width of the dark and light stripes.

32. The apparatus according to claim 17, and further comprising:

inspection area gating means receiving said photoelectrically converted image and connected to said judging means for dividing said image transmitted through said bottle into a plurality of discrete inspection areas, said inspection area gating means comprising a plurality of gates associated with and corresponding to said plurality of discrete inspection areas for controlling said defect detection means to inspect particular ones of said discrete inspection areas.

33. The apparatus according to claim 17, and further comprising:

monitor display means comprising a memory and visual display means, said monitor display means receiving said photoelectrically converted image and information related to said defect point for displaying said photoelectrically converted image and said defect point on said visual display and storing said photoelectrically converted image and said defect point in said memory.

34. The apparatus according to claim 17, and further comprising:

masking means connected to said defect detection means and said judging means for defining a particular region for detecting defects in a bottle so that at least a predetermined number of defect points must be detected in said particular region for declaring a bottle defective.

35. A method for inspecting the sidewalls of bottles comprising the steps of:

illuminating the sidewall of a bottle with light in a pattern of alternating shadowed and illuminated stripes to transmit an image of alternating dark and light stripes through the sidewall of a bottle;

photoelectrically converting said image transmitted through the sidewall of the bottle to an image signal;

scanning the image signal along a scan line in a direction transverse to the dark and light stripes;

sensing the brightness at at least three points along said scan line at any instant of time, said at least three points comprising a central point and first and second outer points on opposite sides, respectively, of said central point;

comparing the brightness at said central point with the brightness of said first and second outer points; and designating the central point a defect point if the brightness of the central point differs from the brightness of each of said first and second outer points by at least a preset value.

36. The method of claim 35, wherein said step of designating the central point a defect point designates the central point a defect point when the brightness of the central point is greater than the brightness of each of said first and second outer points by at least said preset value, or when the brightness of the central point is less than the brightness of each of said first and second outer points by at least said preset value.

37. the method of claim 35, and further comprising the steps of:

selecting first and second sets of points along said scan line, said first set of points being on one side of said central point and said second set being on the other side of said central point;

performing the step of comparing said central point with respect to each point in said first set and a similarly positioned point in said second set;

performing said step of designating a point a defect point with respect to each point in said first and second sets;

further designating said central point a defect point with respect to said first and second sets of points if said central point is determined to be a defect point with respect to any one of said points in said first and second sets.

38. An apparatus for inspecting the sidewalls of bottles comprising:

illuminating means for illuminating the sidewall of a bottle with light in a pattern of alternating shadowed and illuminated stripes to transmit an image of alternating dark and light stripes through the sidewall of a bottle;

photoelectrically converting means for photoelectrically converting said image transmitted through the sidewall of the bottle to an image signal;

scanning means for scanning the image signal along a scan line in a direction transverse to the dark and light stripes;

sensing means for sensing the brightness at at least three points along said scan line at any instant of time, said at least three points comprising a central point and first and second outer points on opposite sides, respectively, of said central point;

comparing means for comparing the brightness at said central point with the brightness of said first and second outer points; and designating means for designating the central point a defect point if the brightness of the central point differs from the brightness of each of said first and second outer points by a preset value.

39. The apparatus of claim 38, wherein said designating means designates the central point a defect point when the brightness of the central point is greater than the brightness of each of said first and second outer points by at least said preset value, or when the brightness of the central point is less than the brightness of each of said first and second outer points by at least said preset value.

40. The apparatus of claim 39, and further comprising means for selecting first and second sets of points along said scan line, said first set of points being on one side of said central point and said second set being on the other side of said central point;

said comparing means comparing said central point with respect to each point in said first set and a similarly positioned point in said second set; and said designating means designating the central point a defect point with respect to each point in said first and second sets if said central point is determined to be a defect point with respect to any one of said points in said first and second sets.

* * * * *